US006398750B1

(12) United States Patent
Quinn et al.

(10) Patent No.: US 6,398,750 B1
(45) Date of Patent: Jun. 4, 2002

(54) ANKLE BRACE

(76) Inventors: Patrick J. Quinn, 762 Camberwell Dr., Eagan, MN (US) 55123; Gregory A. Hoistad, 7101 W. 113 St., Bloomington, MN (US) 55438

( * ) Notice: Subject to any disclaimer, the term of this patent is extended or adjusted under 35 U.S.C. 154(b) by 0 days.

(21) Appl. No.: 09/430,007

(22) Filed: Oct. 29, 1999

(51) Int. Cl.[7] .............................. A61F 13/00; A61F 5/00
(52) U.S. Cl. .......................................... 602/65; 602/27
(58) Field of Search ................................ 602/5, 23, 27, 602/65, 60–63, 28–29; 128/882

(56) References Cited

U.S. PATENT DOCUMENTS

| 1,374,669 A | 4/1921 | McClellan | |
|---|---|---|---|
| 2,450,862 A | 10/1948 | Wilkinson | 128/80 |
| 3,327,410 A | 6/1967 | Park, Sr. et al. | 36/2.5 |
| 3,613,273 A | 10/1971 | Marquis | 36/2.5 |
| 3,674,023 A | 7/1972 | Mann | 128/166 |
| 3,970,083 A | 7/1976 | Carrigan | 128/166 |
| 4,133,311 A | 1/1979 | Karczewski | 128/166 |
| 4,323,058 A | 4/1982 | Detty | 128/80 |
| 4,527,556 A | 7/1985 | Nelson | 128/80 |
| 4,869,267 A | 9/1989 | Grim et al. | 128/80 |
| 4,878,504 A | 11/1989 | Nelson | 128/80 |
| 5,067,486 A | 11/1991 | Hely | 128/80 |
| 5,217,431 A | * 6/1993 | Toronto et al. | 602/27 |
| 5,445,598 A | * 8/1995 | Nguyen-Senderowicz | 602/65 |
| 5,795,316 A | * 8/1998 | Gaylord | 602/27 |
| 5,899,872 A | * 5/1999 | Gilmour | 602/27 X |
| 6,117,098 A | * 9/2000 | Weber et al. | 602/27 |

OTHER PUBLICATIONS

StrapLok® Brochure; Swede–O, Inc; 12/98; 1 pg.

* cited by examiner

Primary Examiner—Denise M. Pothier
(74) Attorney, Agent, or Firm—Mau & Krull, P.A.

(57) ABSTRACT

An ankle support (10) includes a first portion which is a boot-like member (11) A preconfigured figure 8 member comprising a first strap (40) and a second strap (50) is positioned around the boot-like member. An outer member (30) is secured to the boot-like member and forms a cover to hold the preconfigured figure 8 member in place to prevent misalignment of the straps (40 and 50).

14 Claims, 4 Drawing Sheets

ANKLE BRACE

BACKGROUND OF THE INVENTION

1. Field of the Invention

This invention relates generally to an ankle brace and more particularly to an ankle brace having an internal figure 8 formed from two straps.

2. Description of the Prior Art

Providing ankle supports for athletes engaging in various sporting activities is well known. This protection supports the ankle in such a manner to lock the heel against turning, as this may cause the ankle to be strained or sprained. Various forms of protection are used to prevent injuries in addition to providing protective support for ankles that have already been injured.

Ankle braces, such as those shown in U.S. Pat. No. 4,527,556 provide an easy-to-use brace for supporting the ankle. Also, a heel may be locked in place by the use of adhesive taped to securely tape the ankle. This is done in a "figure 8"pattern. There are a number of disadvantages in using tape. One of the major disadvantages is a large cost that is associated with taping an ankle each day. Other disadvantages include slippage when the wearer perspires, loosens after use, the development of calluses on the foot and ankle and having to clean the ankle or foot after the tape is removed. Elastic bandages have been used, but these do not provide as much support as the adhesive tape. Other ankle braces, such as those shown in U.S. Pat. No. 5,067,486 utilize an ankle brace that also incorporates two straps which may be wrapped around the brace in the form of a figure 8. The use of such straps in conjunction with ankle braces is known as is further shown in U.S. Pat. No. 3,073,305.

One of the major disadvantages with the braces which incorporate such straps is that the straps are always loose and easily become entangled. This is especially true with the common use of Velcro®-type fasteners where the fastening ends of the straps may become attached to any portion of the brace or a duffel bag in which they may be stored. This provides a great source of frustration when using the brace. When the brace is taken off, the straps are in disarray and it is cumbersome and time-consuming to straighten out the straps so that they may later be wrapped around the ankle. Further, the user has to position the straps correctly.

The present invention addresses the problems associated with the prior art and provides for an easy-to-use ankle brace which incorporates a preconfigured figure 8 strap.

SUMMARY OF THE INVENTION

The present invention is an ankle support for use in supporting an ankle bone and ankle joint. The support includes a boot-like member having a sleeve portion for receiving a foot and an ankle. The boot-like member is securable around the foot and ankle. A preconfigured figure 8 member has first and second straps. The first strap has a first end and a second end. The first end is secured to the boot-like member and the first strap is positioned over the top of the boot-like member and under the ankle and extending back up the first side. The second end of the first strap is releasably secured to the first side. The second strap has a first end and a second end also. The first end is secured to the boot-like member and the second strap is positioned over the top of the boot-like member and under the ankle and extends back up the second side. The second end of the strap is releasably secured to the second side. An attachment is positioned to keep the first and second straps positioned proximate the boot-like member. The attachment is positioned between the first and second ends of the straps, wherein a preconfigured figure 8 is formed by the first and second straps and the attachment maintains the straps in position.

In another embodiment, the invention is an ankle support for use in supporting an ankle bone and ankle joint. The support includes a boot-like member having a sleeve portion for receiving a foot and an ankle. The boot-like member is securable around the foot and ankle. The boot-like member has a top and back. A preconfigured figure 8 member has first and second straps. The first strap has a first end and a second end. The first end is secured to the boot-like member and the first strap is positioned over the top of the boot-like member and under the ankle and extending back up the first side. The second end of the strap is releasably secured to the first side. The second strap has a first end and a second end. The first end is secured to the boot-like member and the second strap is positioned over the top of the boot-like member and under the ankle and extending back up the second side. The second end of the second strap is releasably secured to the second side. An outer member is secured to the boot-like member. The outer member forms a cover to hold the preconfigured figure 8 member in place and prevent misalignment of the straps of the figure 8 member.

DETAILED DESCRIPTION OF THE PREFERRED EMBODIMENT

Figure 1:
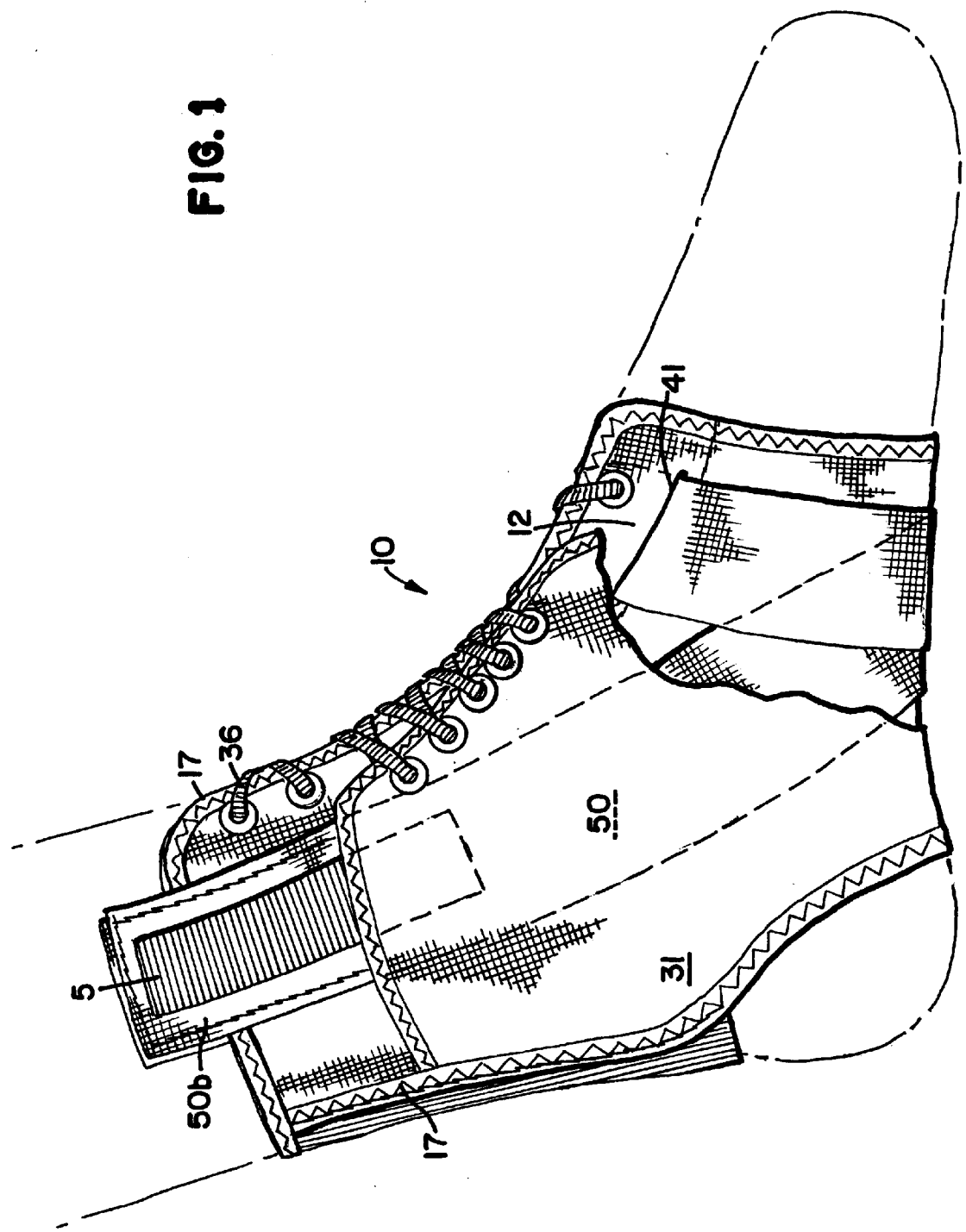
FIG. 1 is a side elevational view of the support brace incorporating the present invention.
Figure 2:
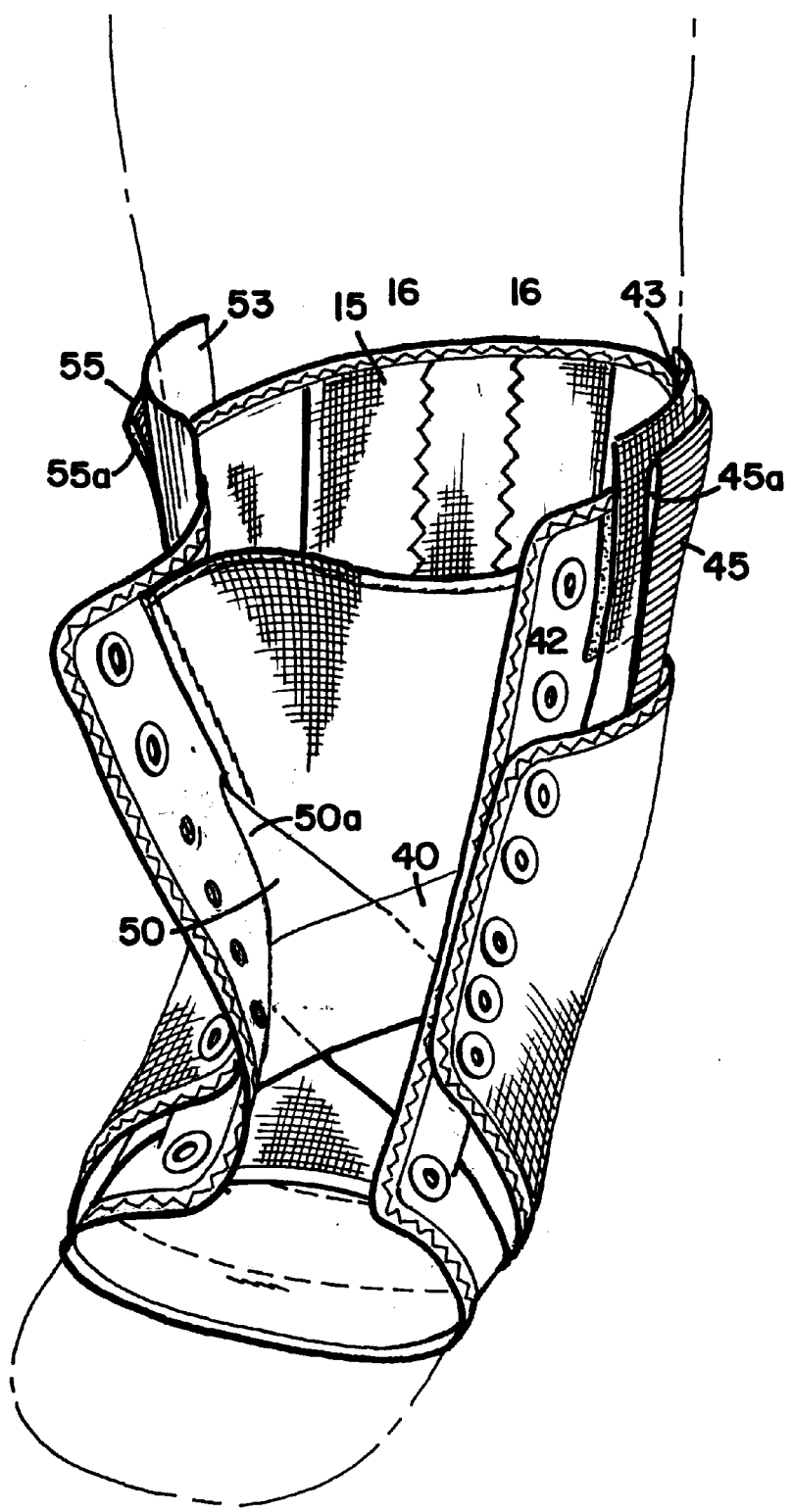
FIG. 2 is a perspective view generally viewed from the front of the support brace of FIG. 1.

Referring to the drawing, wherein like numerals represent like parts throughout the several views, there is generally disclosed at 10 an ankle support. The ankle support 10 has a first portion 11 and an outer member 30. The first portion 11 and outer member 30 may be made of suitable material such as 840 denier nylon or a combination nylon and polymesh covered with a vinyl coating. Further, a suitable foam padding material may be laminated to the first portion 11 and would be positioned proximate the inner side which comes in contact with the leg or ankle. The first portion 11 forms a bootleg member which encircles the ankle to be supported. The first portion 11 has a right side 12 and a left side 13. It is preferably formed from a one-piece material. The right side 12 is operatively connected to the left side 13 at the front by a stretchable mesh tongue 14. The mesh tongue is connected to the first portion 11 by suitable means such as stitching. The rear portion of the right side 12 and left side 13 is connected by an elastic member 15 by suitable means such as stitching 16. The elastic member 15 provides for some expansion between the spaced apart back edges of the right side 12 and left side 13. A binding 17 is secured around the periphery of the first portion 11. The binding may be of suitable material such as a polyester binding tape. A plurality of openings 18 are formed along the front portion of the right side 12 and left side 13. Eyelets 19 are secured to the top two and bottom two openings 18. The first portion 11 forms three openings. The first opening 20 is positioned proximate the toes of the user. The second opening 21 is the heel opening. The third opening 22 is formed at the top of the first portion 11. The third opening is formed for the lower part of the leg of the user.

Figure 4:
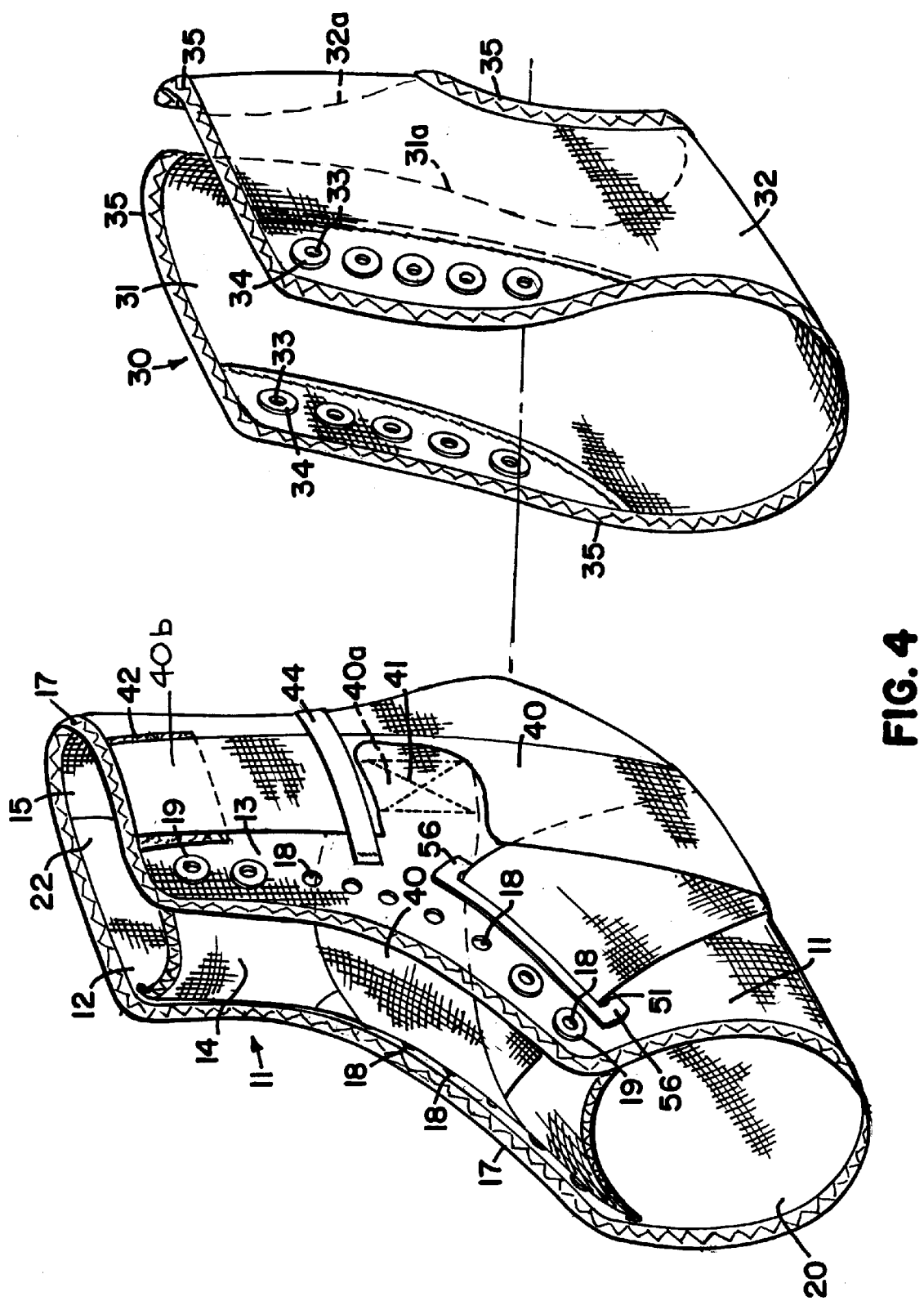
FIG. 4 is an exploded perspective view showing the support brace of FIG. 1.

The outer member 30, as most clearly shown in FIG. 4, has a right side 31 and a left side 32. At the front of both the right side 31 and left side 32 are formed a plurality of openings 33 around which eyelets 34 are secured. A binding 35 is secured, by suitable means such as stitching to the top and front of right sides 31 and 32. The bottom U-shaped portion of the back also has binding 35 secured thereto. The upper rear edges 31a and 32a of right side 31 and left side 32 are secured to the first portion 11 by stitching. They are secured to the first portion 11 before the binding 17 is applied to the back side of the right side 12 and left side 13. This therefore secures the back side of the outer member 30 to the first portion 11. The front portion of the outer member 30 and first portion 11 are operatively connected by means of laces 36. Preferably, the eyelets 34 are slightly offset from the openings 18 to provide a more secure fit as taught by U.S. Pat. No. 4,527,556. The ankle support 10 described so far is typical of a prior art ankle support already available.

The present invention also provides a preconfigured or internal figure 8 member which includes two straps in an ankle support design. The preconfigured figure 8 straps include a first strap 40 which has a first end 40a secured to the inside surface of the left side 13 by suitable means such as stitching 41. The first strap 40 is then positioned between the inside surface of the left side member 13 and the mesh tongue 14. The first strap 40 is in position before the tongue 14 is secured to the left side. Therefore, when the tongue is stitched to the left side 13, the strap 40 is also stitched between the tongue 14 and left side 13. The first strap 40 then continues over the top portion of the foot and goes through a slot 51 which is formed in the right side 12, at a position just slightly above the position where the tongue 14 and right side 12 are joined. The by suitable means such as stitching 16. The elastic member 15 provides for some strap 40 then goes underneath the foot and back up the left side 12. A rectangular pad of hook material 42 is sewn to the left side 13 proximate the top of the left side 13. A loop material 43 is sewn to the inside surface of the second end 40b of the strap 40. The loop material 43 and hook material 42 provide for a releasable connection between the second end 40b of the strap 40 and the left side 13. The hook and loop material may be any suitable material such as Velcro(g material, which is well known in the art. It is of course understood that other suitable means for releasably connecting the strap 40 may be utilized. An additional strap 44 is secured to the left side 13 by suitable means such as stitching. The strap 44 forms a loop through which the second end 40b is inserted and is used as an additional guide. The strap 44 is at an elevation which is approximately one inch below the top of the left side 32 of the outer member 30. Optionally, a tab 45 may be utilized. The tab 45 is secured at its bottom to the strap 40 and is free to move away from the strap 40 at the tab's top end. At the top end of the tab 45 is an opening 45a through which a user may insert their fingers. The tab 45 is used to assist in pulling up the strap 40. However, it is appreciated that the tab 45 is optional and the user may simply pull up on the second end 40b of the first strap 40 to tighten the first strap 40. For clarity in viewing FIG. 4, the tab 45 has not been shown in FIG. 4.

The preconfigured figure 8 member also includes a second strap 50 which has a first end 50a secured to the inside surface of the right side 12 by stitching (not shown). It is secured in the same manner as the first end 40a of the first strap 40. The second strap 50 is then positioned between the inside surface of the right side member 12 and the mesh tongue 14. The second strap 50 is in position before the tongue 14 is secured to the right side. Therefore, when the tongue is stitched to the right side 12, the strap 50 is also stitched between the tongue 14 and right side 12. The second strap 50 then continues over the top portion of the foot an goes through a slot 51 which is formed in the left side 13, at a position just slightly above the position where the tongue 14 and left side 13 are joined. The strap 50 is underneath the strap 40 when the straps cross at the top, as shown in FIG. 4. The strap 50 then goes underneath the foot and back up the right side 12. A rectangular pad of hook material, not shown, but similar to material 42 is sewn to the right side 12 proximate the top of the right side 12. A loop material 53 is sewn to the inside surface of the second end 50b of the strap 50. The loop material 53 and hook material provide for a releasable connection between the second end 50b of the strap 50 and the right side 12. The hook and loop material may be any suitable material such as Velcro® material, which is well known in the art. It is of course understood that other suitable means for releasably connecting the strap 50 may be utilized. An additional strap, not shown, but similar to strap 44 is secured to the right side 12 by suitable means such as stitching. The strap forms a loop through which the second end 50b is inserted and is used as an additional guide. The strap is at an elevation which is approximately one inch below the top of the right side 31 of the outer member 30. Optionally, a tab 55 with an opening 55a may be used. The tab 55 is the same as tab 45 and so it will not be described further. However, it is appreciated that the tab is optional and the user may simply pull up on the second end 50b of the second strap 50 to tighten the first strap 50. A plastic loop guide 56 is secured to the outer side of the left side 13. The guide 56 has a slot which is positioned over the slot 51. The guide 56 prevents bunching of the support 10 from the force of the strap 50. A similar guide (not shown) is used proximate slot 41. The loop guide 56 helps prevent bunching up the straps 40 and 50 at the top of the brace, proximate the guides, when a pulling force is applied to the second ends 40a and 50a.

While it is preferred that the straps 40 and 50 be secured at their first ends to the side, it is understood that with other designs or other boot-like members, the first ends may be attached elsewhere, such as at the front or back. The first ends are secured at approximately the same height, which is proximate the malleoli, recognizing that the medial malleoli is higher than the lateral malleoli.

The first and second straps 40 and 50 form a preconfigured figure 8 which is held in position by the outer member 30. The straps 40 and 50 are covered by the outer member 30. The outer member 30 prevents the straps from becoming snagged or caught on other objects. Further, it keeps the straps 40 and 50 in a preconfigured figure 8 position. There is therefore no need for the user to apply the straps in a correct configuration since the design of the present invention keeps the straps 40 and 50 in the configuration of a figure 8. The figure 8 configuration effectively locks the heel preventing inversion and eversion sprains. The support 10 is designed so that it may be utilized on either the right or left foot. Extra lateral or medial protection can be obtained by pulling on the strap tighter. That is, pulling the medial strap and then the lateral strap will result in additional lateral protection and vice versa. The straps 40 and 50 are prevented from going out the front of the ankle support 10 by the laces which are laced through the eyelets and holes in the first portion 11 and outer member 30. The sewing of the outer member 30 to the first portion 11 prevents the straps from loosing their configuration by going out the rear of the ankle support 10.

Figure 3:
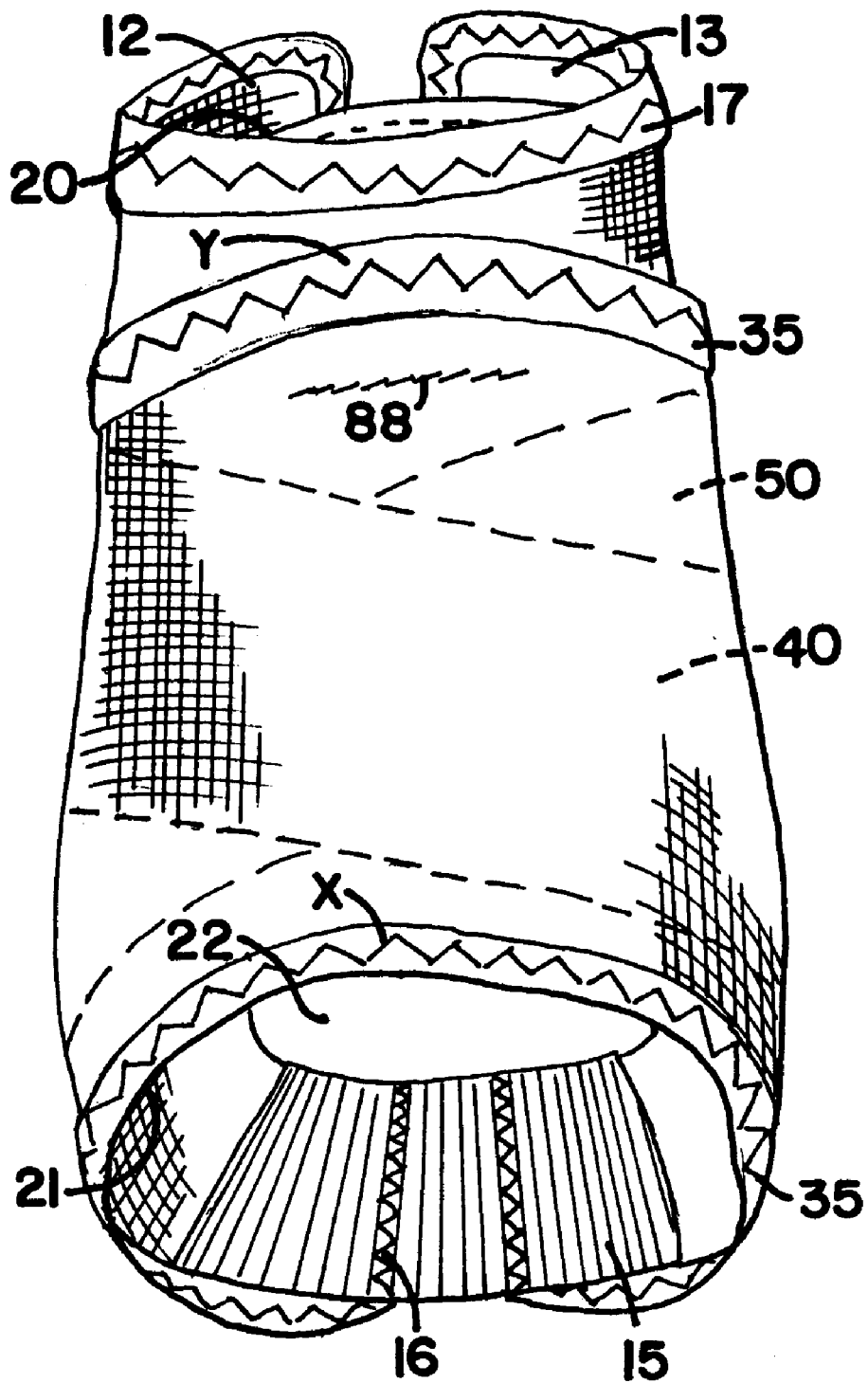
FIG. 3 is a perspective view, shown generally from below, of the support brace of FIG. 1.

While in the preferred embodiment, the outer member 30 is the attachment that preconfigures the straps 40 and 50 into a figure 8 configuration. It is envisioned that other designs would also work. For instance, the first portion 11 alone shown in FIG. 1 does in fact preconfigure the straps in the figure 8 position. The first end of the straps 40*a* and 50*a* are secured to the right or left side respectively by the stitching proximate the tongue 14. Then, the slots 41 and 51 provide another position of confinement to preconfigure the straps 40 and 50. The strap 44 for the first strap 40 and another similar strap (not shown) for the second strap 50 confines the second end 40*b* and 50*b* in the preconfigured configuration of a figure 8. By securing the end of the straps 40*a* and 50*a* to the brace and then having an additional guide (slots 41 and 51) midway through each of the straps 40 and 50 and another attachment (strap 44) proximate the second ends 40*b* and 50*b* of the straps 40 and 50, the straps 40 and 50 stay in their preconfigured figure 8 position. Further, the straps 40 and 50 are held in their preconfigured configuration at the bottom of the ankle support 10 by being secured between the bindings 35 between the first portion II and the outer member 30. The bindings 35 at positions X and Y as shown in FIG. 3 are stitched to the first portion 11 thereby capturing the straps 40 and 50. The binding 35 is secured around the outer member 30 and for a distance of approximately two inches, at position X and Y, is stitched to the first portion 11. Additional stitching 88 may be used to secure the outer member 30 to the first portion 11, thereby further confining the straps 40 and 50.

While the ankle support 10 is shown as being closed by means of laces 36, it is envisioned that lace eyelets, hook/loop closures or other suitable closures may also be utilized. The straps 40 and 50 may be of a thin strong relatively non-stretchable material such as a 430 denier nylon or webbing, but could also be a material that has stretch if desired. The second ends 40*b* and 50*b* are preferably secured above the malleoli on both sides. The first ends 40*a* and 50*a* are preferably sewn or permanently attached. However, they may be releasably connected by use of Velcro® or other suitable means. The straps 40 and 50 are typically tightened to the desired tightness before the laces 36 are tightened. Also, a more standard tongue, attached only at its base, may be used as in other existing ankle braces.

By having the straps 40 and 50 in their preconfigured figure 8 position, the user is able to concentrate on only securing the straps 40 and 50 to the desired tightness. The design of the straps, such that the second ends 40*b* and 50*b* are pulled upward, provides for a efficient and effective method of securing the straps 40 and 50 at the desired tension via the hook and loop materials 42 and 43.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An ankle support for use in supporting an ankle bone and ankle joint, comprising:
 a) a boot-like member having a sleeve portion for receiving a foot and an ankle, the boot-like member having a first side and a second side, the boot-like member securable around the foot and ankle;
 b) a preconfigured figure eight member, the preconfigured member having first and second straps;
 c) the first strap having a first end and a second end, the first end secured to the boot-like member and the first strap positioned over the top of the boot-like member adapted and configured to be positioned under the ankle and extending back up the first side;
 d) the second end of the first strap releasably secured to the first side;
 e) the second strap having a first end and a second end, the first end secured to the boot-like member and the second strap positioned over the top of the boot-like member and adapted and configured to be positioned under the ankle and extending back up the second side;
 f) the second end of the second strap releasably secured to the second side; and
 g) an attachment operatively connected to the boot-like member, the attachment member positioned to keep the first and second straps positioned proximate the boot-like member, the attachment positioned between and intermediate the first and second ends of the straps, wherein a preconfigured figure eight is formed by the first and second straps and the attachment maintains the straps in position prior to being securable around the ankle bone and joint, the first and second straps remain in a preconfigured figure eight configuration during application of the ankle support.

2. The support of claim 1, further comprising a first and second tab operatively connected to the first and second strap's second ends respectively, wherein the tabs may be pulled upward to provide tension to the straps before the straps are secured to the boot-like member.

3. The support of claim 1, wherein the first ends are permanently secured to the boot-like member.

4. The support of claim 1, wherein either of the second ends may be secured to the boot-like member to protect for inversion or eversion.

5. The support of claim 1, wherein the first end of the first strap is secured to the first side of the boot-like member and the first end of the second strap is secured to the second side of the boot-like member.

6. The support of claim 1, further comprising a plurality of eyelets formed in the boot-like member proximate the first and second sides and laces operatively connected to the eyelets to secure the boot-like member to the foot.

7. The support of claim 1, further comprising slots formed in the boot-like member and the straps extending through the slots, and guides, each having a slot, positioned over the slots of the boot-like member.

8. An ankle support for use in supporting an ankle bone and ankle joint, comprising:
 a) a boot-like member having a sleeve portion for receiving a foot and an ankle, the boot-like member having a first side and a second side, the boot-like member securable around the foot and ankle, the boot-like member having a top and back;
 b) a preconfigured figure eight member, the preconfigured member having first and second straps;
 c) the first strap having a first end and a second end, the first end secured to the boot-like member and the first strap positioned over the top of the boot-like member adapted and configured to be positioned under the ankle and extending back up the first side;
 d) the second end of the first strap releasably secured to the first side;
 e) the second strap having a first end and a second end, the first end secured to the boot-like member and the second strap positioned over the top of the boot-like member and adapted and configured to be positioned under the ankle and extending back up the second side;

f) the second end of the second strap releasably secured to the second side; and g) an outer member secured to the boot-like member, the outer member forming a cover to hold the preconfigured figure eight member in place and prevent misalignment of the straps of the figure eight member prior to being secured around the ankle bone and joint and the cover positioned between and intermediate the first and second ends of the straps, the first and second straps remain in a preconfigured figure eight configuration during application of the ankle support.

9. The ankle support of claim 8, further comprising a first and second tab operatively connected to the first and second strap's second ends respectively, wherein the tabs may be pulled upward to provide tension to the straps before the straps are secured to the boot-like member.

10. The ankle support of claim 8, wherein the first ends are permanently secured to the boot-like member.

11. The ankle support of claim 8, wherein either of the second ends may be secured to the boot-like member to protect for inversion or eversion.

12. The ankle support of claim 8, wherein the first end of the first strap is secured to the first side of the boot-like member and the first end of the second strap is secured to the second side of the boot-like member.

13. The ankle support of claim 8, further comprising a plurality of eyelets formed in the boot-like member proximate the first and second sides and laces operatively connected to the eyelets to secure the boot-like member to the foot.

14. The ankle support of claim 8, further comprising slots formed in the boot-like member and the straps extending through the slots, and guides, each having a slot, positioned over the slots of the boot-like member.

* * * * *